United States Patent [19] [11] Patent Number: 5,043,457
Lee [45] Date of Patent: Aug. 27, 1991

[54] 2(5H)-FURANONES SUBSTITUTED IN THE 3 POSITION, AS CA²⁺ CHANNEL ANTAGONISTS AND ANTI-INFLAMMATORY AGENTS

[75] Inventor: Gary C. M. Lee, Laguna Hills, Calif.

[73] Assignee: Allergan, Inc., Irvine, Calif.

[21] Appl. No.: 510,367

[22] Filed: Apr. 17, 1990

[51] Int. Cl.⁵ .................. C07F 9/06; C07D 305/12
[52] U.S. Cl. .................. 549/222; 514/471; 514/473; 549/214; 549/321; 549/323
[58] Field of Search ............ 549/222, 321, 323, 214; 514/471, 473

[56] References Cited

U.S. PATENT DOCUMENTS

| 2,359,096 | 9/1944 | Elderfield | 260/239.5 |
| 2,359,208 | 9/1944 | Elderfield | 260/344 |
| 4,447,455 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |

FOREIGN PATENT DOCUMENTS

| 133376 | 2/1985 | European Pat. Off. |
| 209274 | 1/1987 | European Pat. Off. |
| 295056 | 6/1987 | European Pat. Off. |

OTHER PUBLICATIONS

Bonjouklian, et al., Chemical Abstracts, vol. 106, 156260c, p. 670 (1987).
Reynolds, et al. J. Am. Chem. Soc., 110, pp. 5172–5177 (1988).
Tocanne et al., Chemical Abstracts 69 76581k, p. 7146 (1968).
Deems, et al., Biochimica et Biophysica Acta, 917, pp. 258–268 (1987).
Scheuer et al., Journal of the American Chemical Society 100:1, p. 307 (Jan., 4, 1978).
Graziano, et al., Chemical Abstracts 107, (1987), 236559t.
Negishi et al., J. Org. Chem 45, pp. 5223–5225, (1980).

Primary Examiner—Cecilia Shen
Attorney, Agent, or Firm—Gabor L. Szekeres; Martin A. Voet; Robert J. Baran

[57] ABSTRACT

Compounds of the formula

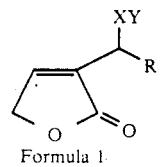

Formula 1 in which R is alkyl, arylalkyl or substituted arylkalkyl, or alkenyl containing one or more olephinic bonds; X is O, NH or NR₁, where R₁ is alkyl of 1 to 20 carbons or arylalkyl; and Y is H, alkyl of 1 to 20 carbons, arylalkyl, aryl, substituted aryl, substituted arylalkyl, alkenyl containing one or more olephinic bonds PO(OH)₂, PO(OH)OR₂, PO(OH)R₂ PO(OR₂)₂, where R₂ is independently alkyl of 1 to 20 carbons, phenyl, or substituted phenyl, further Y is CO—R₃, CO—OR₃, CONHR₃, SO₂R₃, SO₂NHR₃, (CH₂)ₙ—O—R₃, or (CH₂)ₙ—O—(CH₂)ₘ—O—R₃, where n, and m, are integers and are independently 1 to 20 and R₃ is H, alkyl, alkenyl containing one or more olephinic bonds, aryl, substituted arylalkyl or substituted arylalkyl, with the proviso that when Y is CO—R₃, CO—OR₃, and CONHR₃ then R₃ is not hydrogen, are disclosed. The compounds are Ca²⁺ channel antagonist, have weak or no activity as inhibitors of phospholipase A₂, and are anti-inflammatory agents.

32 Claims, No Drawings

2(5H)-FURANONES SUBSTITUTED IN THE 3 POSITION, AS CA²⁺ CHANNEL ANTAGONISTS AND ANTI-INFLAMMATORY AGENTS

BACKGROUND OF THE INVENTION

1. Field of the Invention

The present invention is directed to novel 2(5H)-furanones substituted in the 3 position with alpha hydroxy or alpha amino substituted alkyl or aralkyl groups, which compounds are active as anti-inflammatory agents. The present invention is also directed to pharmaceutical compositions which comprise one or more of the novel compounds of the invention, to the methods of using these pharmaceutical compositions, and to the chemical processes of making the novel compounds.

2. Brief Description of the Prior Art

Manoalide is a compound isolated from a marine sponge [E. D. de Silva et al., *Tetrahedron Letters* 21:1611-1614 (1980)] which has anti-inflammatory, immunosuppressive and analgesic properties. Manoalide (Compound 1) the structure of which is shown below, includes a 5-hydroxy-2(5H)-furanone moiety, attached in the 4-position of the furanone ring to the rest of the molecule. Certain analogs of manolide, such as seco-manoalide (Compound 2) dehydro-seco-manoalide (Compound 3) also have anti-inflamatory activity. For further description of the biological of manoalide and some of its derivatives reference is made to U.S. Pat. Nos. 4,447,445, 4,786,651, 4,789,749 and to European Patent Application No. 0 133 376 (published on Feb. 20, 1985).

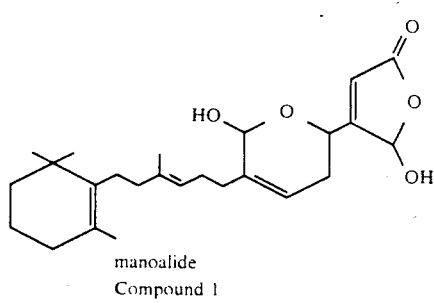

manoalide
Compound 1

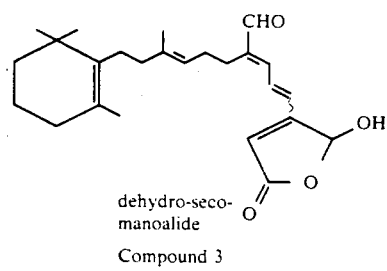

dehydro-seco-manoalide
Compound 3

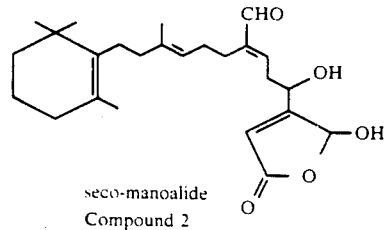

seco-manoalide
Compound 2

Synthetic analogs of manoalide, particularly analogs having various substituents on the furanone moiety of manoalide, are described in several applications for United States Letters Patent by the same inventor as in the present application, the following of which have been allowed and are expected to issue as United States Letters Patent:

Ser. No. 259,225 filed on Oct. 18, 1988;
Ser. No. 281,126 filed on Dec. 7, 1988.

Published European Patent Application No. 0 295 056 discloses 4-substituted 5-hydroxy-2(5H)-furanones having anti-inflammatory, immunosuppressive and anti-proliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

SUMMARY OF THE INVENTION

The present invention covers compounds of Formula 1,

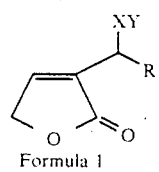

Formula 1 where

R is alkyl, arylalkyl or substituted arylkalkyl, or alkenyl containing one or more olephinic bonds;

X is O, NH or $NR_1$, where $R_1$ is alkyl of 1 to 20 carbons or arylalkyl;

Y is H, alkyl of 1 to 20 carbons, arylalkyl, aryl, substituted aryl, substituted arylalkyl, alkenyl containing one or more olephinic bonds, $PO(OH)_2$, $PO(OH)OR_2$, $PO(OH)R_2$ $PO(OR_2)_2$, where $R_2$ is independently alkyl of 1 to 20 carbons, phenyl, or substituted phenyl, further Y is $CO-R_3$, $CO-OR_3$, $CONHR_3$, $SO_2R_3$, $SO_2NHR_3$, $(CH_2)_n-O-R_3$, or $(CH_2)_n-O-(CH_2)_m-O-R_3$, where n, and m, are integers and are independently 1 to 20 and $R_3$ is H, alkyl, alkenyl containing one or more olephinic bonds, aryl, substituted aryl, arylalkyl or substituted arylalkyl, with the proviso that when Y is $CO-R_3$, $CO-OR_3$, and $CONHR_3$ then $R_3$ is not hydrogen.

In a second aspect the present invention relates to pharmaceutical formulations comprising one or more compounds of Formula 1 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, rheumatoid arthritis, osteoarrhritis, rheumatic carditis, ocular and dermal inflammatory diseases, autoimmune diseases such as allergic diseases, bronchial asthma and myasthenia gravis, and for suppressing unwanted immune responses and retarding proliferation of cell.

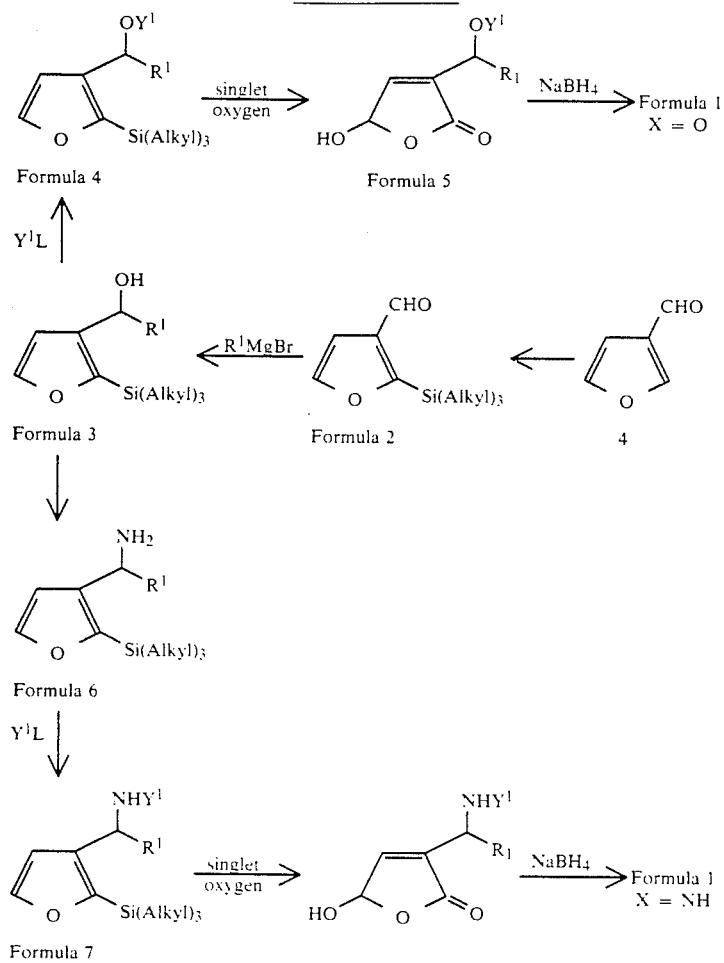

Reaction Scheme 1

In still another aspect, the present invention relates to the processes of making the compounds of Formula 1. In general terms, these processes, shown in a summarized fashion in Reaction Scheme 1, comprise the steps of reacting 3-furaldehyde (Compound 4) with a trialkylsilylchloride, preferably in a regiospecific manner, to yield a 2-trialkylsilyl-3-furaldehyde shown in Formula 2. The 2-trialkylsilyl-3-furaldehyde (Formula 2) is then reacted with a Grignard reagent of the formula R'-MgBr (or the like) to provide a 2-trialkylsilyl-3-(1-hydroxyalkyl)furan of Formula 3. R' is defined as in connection with Formula 1, alternatively R' may be such a precursor of R which can be converted into R by reactions, within the skill of the practicing organic chemist. The 2-trialkylsilyl-3-(1-hydroxyalkyl)furan (Formula 3) is then reacted with a reagent of the formula Y'-L to provide the compounds of Formula 4. In the reagent Y'-L, Y' symbolizes either the Y group (as Y is defined in connection with Formula 1) or such a precursor of the Y group which may be readily converted into Y through reactions within the skill of the practicing organic chemist. L usually symbolizes a leaving group, or such a group which is adapted for the reaction that couples the Y' function to the hydroxyl function in the hydroxyalkyl side chain in the 3-position of the 2-trialkylsilylfuran molecule. L may be a halogen, so that Y'-L may be an alkyl halide or an acylhalide, a chlorophosphate or a sulfonylhalide. L may also be OH, so that the reagant Y'-L is a carboxylic acid which is condensed with the compound of Formula 3 in the presence of dicyclohexylcarbodiimide (DCC) and 4-dimethylaminopyridine (DMAP) (or like reagents) to form an ester. The reagent Y'-L may also symbolize an isocyanate, in which case L symbolizes N=C=O and Y' symbolizes the $R_3$ group as $R_3$ is defined in connection with Formula 1. The 2-trialkylsilyl compounds of Formula 4 are reacted with singlet oxygen to give the 3-substituted 5-hydroxy-2(5H)-furanones of Formula 5. The 5-hydroxy group is "removed" from the compounds of Formula 5 by reduction with sodium borohydride to give compounds of Formula 1 where X is oxygen.

Compounds of Formula 1 where X is NH or $NR_1$ are obtained generally speaking, by first introducing an amino function in the alpha position in the side chain of the 3 position of the 2-triethylsilylfuran molecule. As is shown in Reaction Scheme 1, this can be done by replacing the hydroxyl function of the intermediate 2-trialkylsilyl-3-(1-hydroxyalkyl)furan of Formula 3 with an amino function (for example by reaction with diphenylphosphoryl azide in the presence of diethyl azidodicarboxylate DEAD) followed by a reduction of the azide function to an amino function. The resulting 2-trialkylsilyl-3-(1-aminoalkyl)furan of Formula 6 is thereafter reacted with the reagent Y'-L (as defined above) to give the N-substituted 2-trialkylsilyl-3-(1-aminoalkyl) furan derivatives of Formula 7. The compounds of Formula 7 are oxidized with singlet oxygen to provide the corresponding N-substituted 3-(1-aminoalkyl)-5-hydroxy- 2(5H)-furanone derivatives of Formula 8. The hydroxyl function is removed from the compounds of Formula 8 by reduction with sodium borohydride to yield compounds of Formula 1 where X is NH.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, the term "long chain alkyl" also means the former broad definition of "alkyl" groups but with the restriction that the group has no less than 4 carbon atoms, and no more than approximately 25 carbon atoms.

Unless specifically noted otherwise amides are mono- and di-substituted amides derived from the saturated aliphatic radicals of ten or fewer carbon atoms, or the cyclic or saturated aliphatic-cyclic radicals of 5 to 10 carbon atoms. The compounds of the invention contain a chiral center at the alpha carbon in the side chain on the 3-position of the 2(5H)-furanone moiety. Other compounds of the invention may contain more than one chiral center. Accordingly, the compounds of the invention may be prepared as mixtures of enantiomeric compounds (where the enantiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of in 1:1, or other, ratios. Alternatively, each diastereomeric compound may be sterically and optically pure. However, all of the above-noted forms, including optically pure enantiomers and mixtures thereof, as well as all diastereomers, are within scope of the present invention.

Some of the compounds of the invention may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention, with reference to Formula 1 and with respect to R substituent are those where R is alkyl, preferably long chain alkyl, and even more preferably long chain n alkyl.

With respect to the substituent group X on the alpha carbon of the side chain in the 3-position of the 2(5H)-furanone moiety, the preferred compounds are those where X is O or NH.

With respect to the Y substituent on the hydroxyl or amino function in the side chain in the 3-position of the 2(5H)-furanone moiety, compounds are preferred where Y is H, acyl particularly acetyl. Also preferred are carbamates (where Y is CONHR$_3$) particularly where Y is CONHC$_6$H$_5$, and carbonates (where Y is COOR$_3$) particularly where R$_3$ is lower alkyl, still more preferably ethyl. Compounds of the invention are also preferred where Y is PO(OR$_2$)$_2$ particularly where R$_2$ is lower alkyl, still more preferably ethyl. Other preferred compounds of the invention, with respect to the substituent Y, are those where Y is SO$_2$R$_3$ or (CH$_2$)$_n$—O—(CH$_2$)$_m$—O—R$_3$, more preferably where R$_3$ is lower alkyl, still more preferably methyl.

The most preferred compounds of the invention are those listed below with reference to Formula 9:

| | | | |
|---|---|---|---|
| Compound 5: | X = O | n = 7 | Y = CH$_3$CO; |
| Compound 6: | X = O | n = 11 | Y = H |
| Compound 7: | X = O | n = 11 | Y = CH$_3$CO; |
| Compound 8: | X = O | n = 11 | Y = CONHC$_6$H$_5$; |
| Compound 9: | X = O | n = 11 | Y = COOC$_2$H$_5$; |
| Compound 10: | X = NH | n = 11 | Y = COCH$_3$; |
| Compound 11: | X = NH | n = 11 | Y = SO$_2$CH$_3$. |

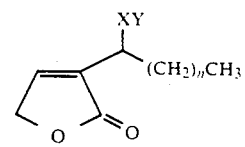

Formula 9

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by the effect on calcium homeostasis. The compounds are calcium channel antagonists. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention differ from manoalide in that they demonstrate weak or no activity as inhibitors of the enzyme phospholipase $A_2$ in vitro or of phosphoinositide-specific phospholipase C.

On the other hand, the compounds of this invention like anoalide, appear to be devoid of the endocrine properties of the glucocorticoids while having anti-inflammatory and immunosuppressive properties.

The compounds of the invention are active in reducing inflammation in the mouse ear anti-inflammatory assay in vivo.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise of Formula 1 and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral Oil | 0-10 |
| Typical pharmaceutical adjuvants | 0-5 |

| Ingredient | Parts by Weight |
| --- | --- |
| Active ingredient | 0.05-5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (mobilization) Inhibition Assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used other cells.

A431 cells were detached using a 5-10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MgSO_4$, 1 mg/ml glucose and 1 mg/ml pyruvate and 1.4 mM calcium (medium A). Approximately $5 \times 10^6$ cells were suspended in medium A and incubated with 4uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340nm and emission wavelength set at 500nm. The cell suspension was continually stirred, maintained at 37° C. and equilibrated for approximately 5 min before addition of various agents. Intracellular calcium ion concentration values ([$Ca^{2+}i$]) were calculated using the following formula:

$$[Ca^{2+}]_i = 220 \times \frac{F - F_{min}}{F_{max} - F}$$

$IC_{50}$ values for the tested compounds were obtained from the intracellular calcium ion concentration values ([$Ca^{2+}$]i), which had been calculated by using the above-referenced formula.

All fluorescence values were measured relative to a EGTA-quenched signal determined as follows: F was the relative fluorescence measurement of the sample. $F_{max}$ was determined by lysing the cells with digitonin (100 ug/ml) in DMSO. After $F_{max}$ was determined the pH was adjusted to 8, with NaOH and $Ca^{2+}$ chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C.G., *Clin Pharmacol Ther* (1974) 16:900-904].

Inhibition of Phospolipase $A_2$

The effect of compounds of this invention on bee venom phospholipase $A_2$ is determined by the following procedure:

a. Bee venom phospholipase $A_2$ in 10 uM HEPES (pH 7.4) with 1 mM $CaCl_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphotidylcholine, 1-palmitoyl-2-mixed (1-$^{14}$C) palmitoyl for 10 min.

c. Start the reaction by the addition of enzyme (0.495 units/ml).

d. Incubation for 15 sec. at 41°.

e. Reaction is terminated by addition of 2.5 ml of isopropanol: n-heptane: 0.5 M $H_2SO_4$ (40:10:1; v:v:v:).

f. 2. m n-heptane and 1.0 ml $H_2O$ added; mixture centrifuged.

g. 2.0 ml n-heptane removed and treated with 200-300 mg of silica gel HR60.

h. Samples centrifuged; 1 ml of n-heptane SN removed and added to 10 ml scintillation fluid.

i. Samples counted on a scintillation counter.

The compounds of the present invention were found to have only weak or no activity in the above described Phospholipase $A_2$ assay.

Inhibition of Phosphoinositide-specific Phospholipase C

The effect of compounds of this invention on phosphoinositide-specific phospholipase C may be determined by procedures described by Bennett et al, *Molecular Pharmacology* 32:587-593 (1987).

The compounds of the present invention were found to have only weak or no activity in the above described Phospholipase C assay.

Activity Data

In the above-described calcium channel (mobilization) inhibition assay the compounds of the invention were found to 50% inhibition ($IC_{50}$) of thyroid releasing hormone (TRH) regulated $Ca^{2+}$ channel activity, and of potassium chloride (KCl) regulated $Ca^{2+}$ activity, respectively, at the following concentrations (in micromoles, ), as indicated in Table 1.

TABLE 1

| | Calcium Channel Inhibition Assay | |
|---|---|---|
| Compound number | $IC_{50}$ (umolar) (TRH regulated) | $IC_{50}$ (umolar) (KCl regulated) |
| 5 | 4.9 | 3.4 |
| 6 | 2 | 1.1 |
| 7 | 16.9 | 0.88 |

SPECIFIC EMBODIMENTS

The compounds of the present invention can be made by the synthetic chemical pathways which are illustrated here in general terms, and in the specific examples as well. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention.

Reaction Scheme 2

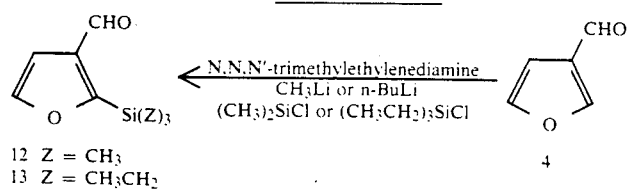

12 Z = $CH_3$
13 Z = $CH_3CH_2$

Reaction Scheme 2

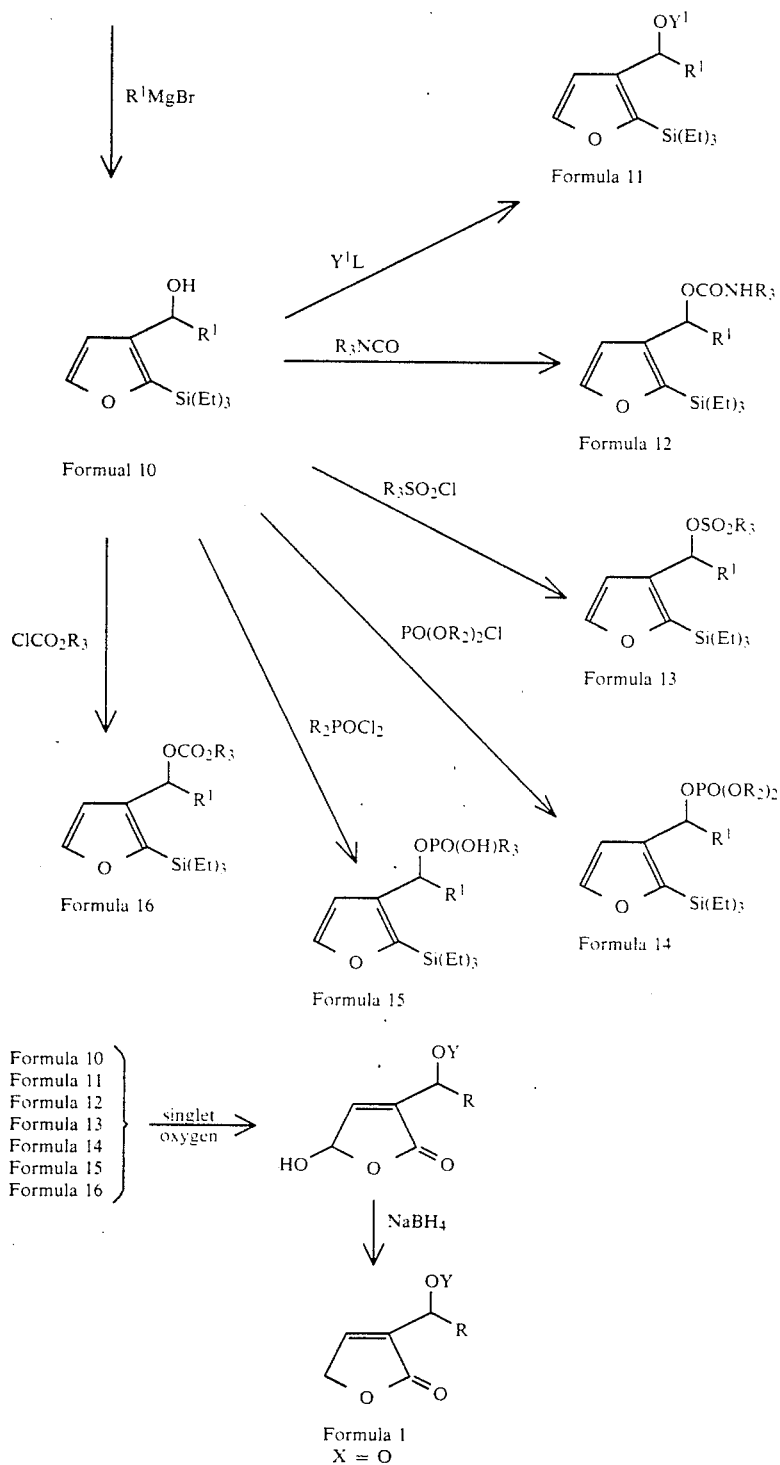

Referring now to Reaction scheme 2, a general process is shown for preparing compounds of the invention which are derivatives of 3-(hydroxyalkyl)-2(5H)-furanone (in Formula 1 X is oxygen). The reaction sequence starts with commercially available 3-furaldehyde (Compound 4) which is reacted in an inert solvent, such as tetrahydrofuran, with an alkyllithium, (n-butyl lithium or more preferably methyl lithium) in the presence of N,N,N-trimethylethylenediamine, and with chlorotrimethylsilane or with chlorotriethylsilane to yield 2-trimethylsilyl-3-furaldehyde (Compound 12) or triethylsilyl-3-furaldehyde (Compound 13), respectively. For simplifying the present description the general reaction sequence is described with primary reference to 2-triethylsilyl-3-furaldehyde (Compound 13), although it should be understood that 2-trimethylsilyl-3-furaldehyde (Compound 12) as well as other 2-trialkylsilyl-3-furaldehydes (Formula 2) are also suitable intermediates for the reaction sequence.

Thus, 2-triethylsilyl-3-furaldehyde (Compound 13) is reacted with a Grignard reagent, (R'-MgBr, R' defined above) or the like, to provide a 2-triethylsilyl-3-(1-hydroxyalkyl)furan of Formula 10. The Grignard reaction is preferably conducted in tetrahydrofuran. Preferred Grignard reagents for this reaction are those derived from long chain alkyl halides (preferably bromides), and particularly from long chain n-alkyl halides.

The 2-triethylsilyl-3-(1-hydroxyalkyl)furan intermediate (Formula 10) is then alkylated with a suitable alkyl halide (or like reagent) to introduce an alkyl group as the Y substituent. order to obtain ester derivatives of 3-(hydroxyalkyl)-2(5H)-furanone the 2-triethylsilyl-3-(1-hydroxyalkyl)furan intermediate (Formula 10) is acylated with a carboxylic acid anhydride (such as acetic anhydride) or with an acyl halide of the formula $R_3COL$ (where L is halogen, preferably chlorine, and $R_3$ is defined as in connection with Formula 1). The ester derivatives can also be obtained through condensation with a carboxylic acid of the formula $R_3COOH$ ($R_3$ defined as in connection with Formula 1) in the presence of dicyclohexylcarbodiimide (DCC) and 4-dimethylaminopyridine (DMAP). The foregoing (and analogous) reactions resulting in alkylation, and more preferably in esterification of the hydroxyl function of the 2-triethylsilyl-3-(1-hydroxyalkyl)furan intermediate (Formula 10) are shown in Reaction Scheme 2, where the reagent capable of performing the alkylation or esterification (alkyl halide, carboxylic acid anhydride, acyl halide, carboxylic acid etc.) is symbolized as Y'-L. The resulting 2-triethylsilyl-3-(1-alkoxyoxyalkyl)furan or 2-triethylsilyl-3-(1-acyloxyalkyl)furan intermediates are generally shown by Formula 11.

In order to obtain the carbamate compounds of the invention in Formula 1 Y is $R_3$—NHCO) the intermediate of Formula 10 is reacted with an isocyanate of formula $R_3CNO$ ($R_3$ defined as in connection With Formula 1). Phenyl isocyanate is a preferred isocyanate for this reaction, which is preferably conducted in presence of copper(2) chloride in dimethylformamide as a solvent. The 2-triethylsilyl-3-(1-carbamoyloxyalkyl)furan derivatives formed as a result of the reaction of the compounds of Formula 10 with an isocyanate are generally shown by Formula 12.

Referring still to Reaction Scheme 2, reaction of the intermediate 2-triethylsilyl-3-(1-hydroxyalkyl)furan of Formula 10 with a sulfonyl halide (preferably sulfonyl chloride) of the formula $R_3SO_2Cl$ ($R_3$ defined as in connection with Formula 1) provides 2-triethylsilyl-3-(1-alkylsulfonyloxyalkyl)furan derivatives of Formula 13. Reaction of the intermediate 2-triethylsilyl-3-(1-hydroxyalkyl)furan of Formula 10 with a chlorophosphate of the formula $PO(OR_2)_2Cl$, or with a phosphonyl dichloride of the formula $R_2POCl_2$ provides the corresponding phosphate or phosphonate derivatives shown by Formula 14 and Formula 15, respectively. Reaction of the intermediate 2-triethylsilyl-3-(1-hydroxyalkyl)furans of Formula 10 with a reagents generally used to introduce an alkoxycarbonyl group, such as ethyl chloroformate (or the like) leads to the corresponding 2-triethylsilyl-3-(1-alkyloxycarbonyloxyalkyl)furan derivatives of Formula 16 ($R_3$ is defined as in connection with Formula 1).

As is shown further in Reaction Scheme 2, the intermediate 2-triethylsilylfuran derivatives of Formula 10 through Formula 16 are converted into the desired 3-substituted 2(5H)furanone derivatives by reaction with singlet oxygen, followed by reduction with sodium borohydride. These reactions, as well as the reaction of the hereinafter described further intermediates with singlet oxygen, are described in detail in connection with several specific examples.

In general terms, the reactions with singlet oxygen are preferably conducted in a mixture of water and tetrahydrofuran, the presence of an initiator, preferably Rose Bengal dye (preferably polymer bounded), which is added to the reaction mixture. The reaction mixture and vessel is flushed with oxygen and the reaction is conducted at low temperature, at approximately $-78°$ C., or for the herein described reactions preferably at approximately 0° C., under a constant positive pressure of oxygen for a number of hours, typically 1 to 7 hours. Most preferably for the herein described reactions, the reaction is conducted for approximately 6 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

The intermediate 3-substituted 5-hydroxy-2(5H)-furanone derivatives are shown by Formula 5 in Reaction scheme 2. These compounds are converted to the desired 3-substituted 2(5H)furanones by reduction with sodium borohydride, as is shown further in Reaction Scheme 2. A theoretical explanation for this reduction (although the present inventor does not wish to be bound by theory) is that the carbon in the 5-position of the 5-hydroxy-2(5H)-furanone molecule is an "aldehydic" carbon which is ring closed with the carboxylic acid group in the "2-position" of the ring, and that the aldehydic carbon is reduced with sodium borohydride to a primary alcohol, which thereafter ring closes to form a "lactone" of Formula 1. Generally speaking, the reduction with sodium borohydride is conducted in an alcohol solvent, preferably in methanol. or more preferably in a mixture of methanol and tetrahydrofuran and the product is typically purified by chromatography on silica gel.

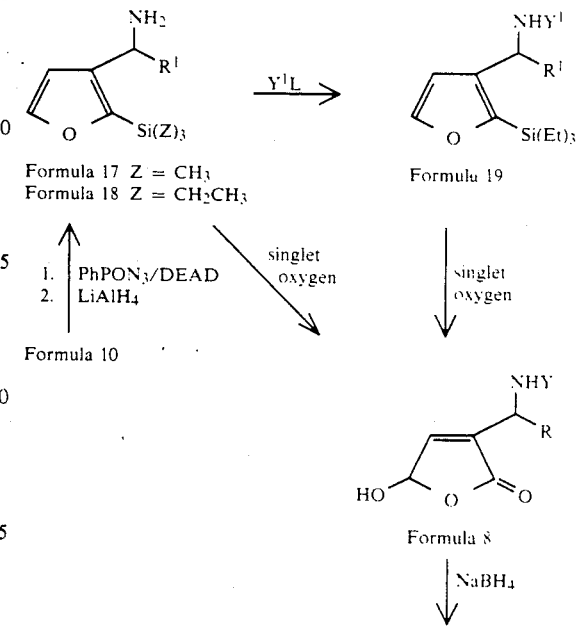

Reaction Scheme 3

Formula 17 Z = $CH_3$
Formula 18 Z = $CH_2CH_3$

Formula 19

1. PhPON$_3$/DEAD
2. LiAlH$_4$

Formula 10

Formula 8

NaBH$_4$

-continued
Reaction Scheme 3

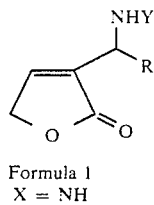

Formula 1
X = NH

Compounds of the invention which are 3-(1-aminoalkyl)-2(5H)furanones or N-substituted derivatives thereof (in other words compounds of the invention where in Formula 1 X is NH) are obtained, generally speaking, in accordance with the reactions shown in Reaction Scheme 3. Thus, 2-trimethylsilyl-3-(1-aminoalkyl)furan compounds (Formula 17) or 2-triethylsilyl-3-(1-aminoalkyl)furan compounds (Formula 18) are alkylated, acylated with a reagent of the formula Y'-L, sulphonylated with a reagent of the formula $R_3SO_2Cl$, reacted with a chlorophosphate of the formula $PO(OR_2)_2Cl$, or with a phosphonyl dichloride of the formula $R_2POCl_2$, to give the corresponding 2-trimethylsilyl- or 2-triethylsilyl 3-(N-substituted 1-aminoalkyl)furans of Formula 19. For the sake of simplifying the ensuing description, in Formula 19 the trialkylsubstituent is shown as triethylsilyl, although it should be understood that other trialkylsilyl substituents are also suitable for this intermediate. Moreover, in Reaction Scheme 3 the reaction Y'-L broadly represents the reagents (such as alkyl halides, carboxylic acid anhydrides, acyl halides, isocyanates, chlorophosphates, dichlorophosphonates, alkylsulfonyl halides etc.) which are capable of introducing the Y function (as defined in connection with Formula 1) into the molecule.

The intermediate 2-triethylsilyl-3-(1-aminoalkyl)furan compounds Formula 18 (or the corresponding 2-trimethylsilyl compounds of Formula 17) can be obtained, as shown in Reaction Scheme 3, from compounds of Formula 10 (or from the corresponding trimethylsilyl derivative) by reaction with diphenylphosphoryl azide in the presence of diethyl azidodicarboxylate DEAD, followed by reduction of the intermediate azide with lithium aluminum hydride.

The 2-triethylsilyl-3-(1-aminoalkyl)furan intermediates (Formula 18) or the 2-triethylsilyl-3-(N-substituted 1-aminoalkyl)furan intermediates (Formula 19) are converted into the corresponding 5-hydroxy-2(5H)-furanone derivatives (Formula 8) by reaction with singlet oxygen. This reaction is described above in connection with Reaction Scheme 2. The 5-hydroxy function is "removed" from the compounds of Formula 8 by reduction with sodium borohydride, as also described above in Reaction scheme 2.

The compounds of the present invention can be made by the synthetic chemical pathways which are illustrated above in general terms, and in the specific examples as well. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention. Therefore, the following examples of specific compounds of the invention, and specific examples of the steps in which the compounds and certain intermediates are made, are set out to illustrate the invention, not to limit its scope.

SPECIFIC EXAMPLES

Example 1

2-Trimethylsilyl-3-furaldehyde (Compound 12)

N,N',N'-Trimethylethylenediamine (9.72 ml, 76 mmol) was added to a solution of n-butyl lithium (a 2.5 M solution in hexane; 30.5 ml, 76 mmol) in tetrahydrofuran (200 ml) at $-78°$ under argon. After 15 minutes, 3-furaldehyde (Compound 4, 6.3 ml, 72.8 mmol) was added, which was followed after 25 minutes by n-butyllithium (32ml, 80 mmol). Even better results (more segioselectivity) are obtained when methyl lithium is used instead of butyl lithium. After another 4 hours, chlorotrimethylsilane (11 ml, 87 mmol) was added. Stirring was continued for 14 hours, while the cooling bath was allowed to warm to room temperature. The mixture was quenched with ice-cold hydrochloric acid and was extracted with ethyl ether. Evaporation of the dried (magnesium sulfate) extracts gave an oil, which was distilled to give the title aldehyde, b.p. $40-1°/0.1$ torr.

$^1H$ NMR ($CDCl_3$) 2.89 (s, 3H), 6.97 (d, 1H, J=1.9 Hz), 7.59 (d, 1H, J=1.9 Hz) and 10.23 (s, 1H).

$^{13}CNMR$ ($CDCl_3$): $-1.89$, 107.7, 137.1, 147.3, 171.1 and 185.7.

Substituting chlorotrimethylsilane with chlorotriethylsilane gave 2-triethylsilyl-3-furaldehyde.

4-(1-Acetoxynonyl)-2-triethylsilylfuran (Compound 14)

A solution of 2-trimethylsilyl-3-furaldehyde (Compound 12, 1.0 g, 5.90 mmol) in tetrahydrofuran (2 ml) was added to a solution of octyl magnesium bromide (11.9 mmol; prepared from 2.30 g 1-bromo octane and 286 mg magnesium turnings) at 0°. After all the aldehyde was consumed in the reaction, as monitored by thin layer chromatography (tlc) acetic anhydride was added and stirring was continued for overnight. Thereafter, the mixture was quenched with dilute hydrochloric acid and was extracted with ether. Evaporation of the dried (magnesium sulfate) extracts gave an oil, which was purified by a silica column using 5% ethyl ether/hexane to give the title furan.

$^1HNMR$ ($CDCl_3$): 0.34 (s, 9H), 0.89 (t, 3H, J=7.2 Hz), 1.27 (br s, 12H), 1.75 (2m, 2H), 2.05 (s, 3H), 5.89 (t, 1H, J =7.3 Hz), 6.45 (d, 1H, J =1.6 Hz) and 7.28 (br s, 1H).

LRMS (m/e, % abundance) 324 (m+, 7), 282(43), 281(88), 267(13), 266(31), 265(15), 169(26), 153(47), 117(100), 75(38) and 73(78).

3(1-Acetoxynonyl)-5-hydroxy-2(5H)-furanone (Compound 15)

A mixture of 3-(1-acetoxynonyl)-2-trimethylsilylfuran (Compound 14, 1.40 g, 4.32 mmol), water ( 5 drops) and Rose Bengal (3 mg) in tetrahydrofuran (20 ml) was exposed to singlet at 0° for 6 hours. The residue, after solvent removal, was purified by a silica column using 50% ethyl ether/hexane to give the title furanone.

$^1HNMR$ ($CDCl_3$): 0.91 (t, 3H, J =7.0 Hz), 1.29 (br s, 12H), 1.85 (m, 2H), 2.15 (s, 3H), 4.20 (br, 1H), 5.60 (m, 1H), 6.14 (br s, 1H) and 7.00 (br s, 1H).

$^{13}CNMR$ ($CDCl_3$): 13.9, 20.8, 22.5, 24.8, 29.0, 29.2, 31.7, 32.6, 32.8, 68.4, 68.7, 96.9, 97.2, 136.7, 145.3, 169.7, 170.6 and 170.8.

HRMS exact mass calculated for $C_{15}H_{25}O_5$ $(M+H)^+$ 285.1702, found 285.1709.

3-(1-Acetoxynonyl)-2(5H)-furanone (Compound 5)

Sodium borohydride (29.3 mg, 0.76 mmol) was added to a solution of 3-(1-acetoxynonyl)-5-hydroxy-2(5H)-furanone (Compound 15, 220 mg, 0.78 mmol) in methanol (1 ml) and tetrahydrofuran (5 ml). Stirring was continued for 14 hours at room temperature and most of the solvent was evaporated. The residue was acidified with ice-cold dilute hydrochloric acid and was extracted with ethyl acetate. Evaporation of the dried (magnesium sulfate) extracts gave an oil, which was purified by preparative silica plates (developed with 60% ethyl ether/hexane) to give the title furanone.

$^1$HNMR (CDCl$_3$) 0.88 (t, 3H, J = 6.5 Hz), 1.25 (m, 12H), 1.85 (m, 2H), 2.11 (s, 3H), 4.82 (m, 2H), 5.61 (t, 1H, J = 6.3 Hz) and 7.29 (t, 1H, J = 1.5 Hz).

$^{13}$CNMR (CDCl$_3$): 14.0, 20.9, 22.6, 24.9, 28.9, 29.1, 29.3, 31.7, 32.6, 6S.9, 70.1, 133.6, 146.1, 169.9 and 171.6.

HRMS exact mass calculated for $C_{15}H_{25}O_4$ $(M+H)^+$ 269.1753, found 269.1735.

Example 2

3-(1-Hydroxytridecyl)-2-triethylsilylfuran (Compound 16)

A solution of dodecylmagnesium bromide (a 1 M solution in tetrahydrofuran; 14.3 ml; 14.3 mmol) was added to a solution of 2-trimethylsilyl-3-furaldehyde (Compound 12, 1.20 g, 7.1 mmol) in tetrahydrofuran (30 ml) at 0°. After all the aldehyde has reacted, as shown by tlc, the mixture was quenched with dilute hydrochloric acid and was extracted with ethyl ether. Evaporation of the dried (magnesium sulfate) extracts gave an oil, which was purified by a silica column using 5% ethyl ether/hexane to give the title furan.

$^1$HNMR (CDCl$_3$): 0.34 (s, 9H), 0.91 (t, 3H, J = 6.9 Hz), 1.28 (br s, 20H), 1.75 (m, 2H), 4.75 (m, 1H), 6.48 (d, 1H, J = 1.7 Hz) and 7.60 (d, 1H, J = 1.7 Hz).

HRMS exact mass calculated for $C_{20}H_{38}SiO_2(M^+)$ 338.2641, found 338.2643.

3(1-Hydroxytridecyl)-5-hydroxy-2(5H)-furanone (Compound 17)

A mixture of 3-(1-hydroxytridecyl)-2-trimethylsilylfuran (Compound 16, 1.17 g, 3.46 mmol), water (5 drops) and Rose Bengal (5 mg) in tetrahydro furan (20 ml) was exposed to singlet oxygen at 0° for 6 hours. The residue, after solvent removal, was purified by a silica column using 60% ethyl ether/hexane to give the title furanone.

$^1$HNMR (CDCl$_3$) 0.90 (t, 3H, J = 7.0 Hz), 1.28 (br s, 20H), 1.75 (m, 2H), 2.85 (br, 1H), 4.50 (br t, 1H), 4.70 (br, 1H), 6.15 (br s, 1H) and 7.06 (br s, 1H).

$^{13}$CNMR (CDCl$_3$): 14.0, 22.6, 25.3, 29.3, 29.4, 29.6, 29.7, 31.9, 35.0, 66.2, 66.5, 97.5, 97.6, 139.8, 145.2, 145.4 and 171.4.

HRMS exact mass calculated for $C_{17}H_{31}O_4$ $(M+H)^+$ 299.2222, found 299.2224.

3-(1-Hydroxytridecyl)-2(5H)-furanone (Compound 6)

Sodium borohydride (31.3 mg, 0.83 mmol) was added to a solution of 3(1-hydroxytridecyl)-5-hydroxy-2(5H)-furanone (Compound 17, 246.9 mg, 0.83 mmol) in methanol (1 ml) and tetrahydrofuran (5 ml). When all the furanone was consumed, most of the solvent was evaporated. The residue was acidified with dilute hydrochloric acid and was extracted with ethyl acetate. Evaporation of the dried (magnesium sulfate) extracts gave an oil, which was purified by preparative silica plates (developed with 60% ethyl ether/hexane) to give the titled furanone.

$^1$HNMR (CDCl$_3$) 0.88 (t, 3H, J = 6.2 Hz), 1.25 (m, 20H), 1.70 (m, 2H), 2.55 (br s, 1H), 4.51 (t, 1H, J = 6.2 Hz), 4.84 (m, 2H) and 7.30 (t, 1H, J = 1.5 Hz).

$^{13}$CNMR (CDCl$_3$): 13.9, 22.5, 25.1, 29.2, 29.3, 29.4, 29.5, 31.8, 35.3, 66.8, 70.4, 136.5, 145.1 and 173.2.

HRMS exact mass calculated for $C_{17}H_{31}O_3(M+H)^+$ 283.2273, found 283.2254.

Example 3

3-(1-Acetoxytridecyl)-2-trimethylsilylfuran (Compound 18)

Dodecylmagnesium bromide (a 1.0 M solution in tetrahydrofuran; 14.3 ml; 14.3 mmol) was added to a solution 2-trimethylsilyl-3-furaldehyde (Compound 12, 1.20 g, 7.1 mmol) in tetrahydrofuran (20 ml). When all the aldehyde was consumed, as monitored by tlc, acetic anhydride (2.02 ml, 21.4 mmol) was added. Stirring was continued at room temperature for 14 hours. The mixture was quenched with water and was extracted with ethyl ether. Evaporation of the dried (magnesium sulfate) extracts gave an oil, which was purified by a silica column using 2% ethyl ether/hexane to give the titled furan.

$^1$HNMR (CDCl$_3$) 0.34 (s, 9H), 0.89 (t, 3H, J = 6.9 Hz), 1.26 (br s, 20H), 1.75 (m, 2H), 2.04 (s, 3H), 5.88 (t, 1H, J = 7.1 Hz), 6.43 (br s, 1H) and 7.58 (br s, 1H).

HRMS exact mass calculated for $C_{22}H_{40}O_3Si(M^+)$ 380.2747 found 380.2752.

3-(1-Acetoxytridecyl]-5-hydroxy-2(5H)-furanone (Compound 19)

A mixture of 3-(1-acetoxytridecyl)-2-trimethylsilylfuran (Compound 18, 1.25 g, 3.29 mmol), water (5 drops) and Rose Bengal (5 mg) in tetrahydrofuran (10 ml) was exposed to singlet oxygen at 0° for 6 hours. The residue, after solvent removal, was purified by a silica column using 50% ethyl ether/hexane to give the title furanone.

$^1$HNMR (CDCl$_3$) 0.93 (t, 3H, J = 6.9 Hz), 1.29 (br s, 20H), 1.85 (m, 2H), 217 (s, 3H), 4.20 (br, 1H), 5.60 (br t, 1H), 6.15 (br s, 1H) and 7.02 (br s, 1H).

$^{13}$CNMR (CDCl$_3$); 14.0, 20.8, 22.6, 24.9, 28.8, 28.9, 29.0, 29.1, 29.3, 29.5, 29.6, 31.5, 31.8, 32.7, 32.8, 68.5, 68.7, 68.8, 96.9, 97.0, 97.2, 136.8, 145.2, 145.3, 169.7, 170.6 and 170.7.

HRMS exact mass calculated for $C_{19}H_{33}O_5$ $(M+H)^+$ 341.2328, found 341.2339.

3-(1-Acetoxytridecyl)-2(5H)-furanone (Compound 7)

Sodium borohydride (251 mg, 0.74 mmol) was added to a solution of 3-(1-acetoxytridecyl)-5-hydroxy-2(5H)-furanone (Compound 19, 251 mg, 0.74 mmol) in methanol (1 ml) and tetrahydrofuran (5 ml) at room temperature. When all the furanone were consumed, as monitored by tlc, the solution was evaporated to dryness. The residue was acidified with dilute hydrochloric acid and was extracted with ethyl acetate. Evaporation of the dried (magnesium sulfate) extracts gave an oil, which was purified by preparative silica plates (developed with 60% ethyl ether/hexane) to give the title furanone.

$^1$HNMR (CDCl$_3$): 0.88 (t, 3H, J = 6.5 Hz), 1.25 (m, 20H), 1.85 (m, 2H), 2.10 (s, 3H), 4.80 (m, 2H), 5.60 (t, 1H, J = 6.0 Hz) and 7.29 (t, 1H, J = 1.6 Hz).

$^{13}$CNMR (CDCl$_3$) 13.7, 20.6, 22.3, 24.7, 28.9, 29.0, 29.1, 29.2, 29.3, 31.6, 32.4, 68.8, 70.0, 133.7, 146.4, 170.2 and 171.9.

HRMS exact mass calculated for C$_{19}$H$_{33}$O$_4$ (M+H)$^+$ 325.2379, found 325.2376.

Example 4

3-(1-Hydroxytridecyl)-2-triethylsilylfuran (Compound 20) is reacted with phenyl isocyanate and copper (2) chloride in dimethylformamide to give 3-(1-phenylcarbamoyloxytridecyl)-2-triethylsilylfuran (Compound 21). Oxidizing the intermediate with singlet oxygen, under similar conditions as in Example 1, and thereafter reduction with sodium borohydride gives 3-(1-phenylcarbamoyloxytridecyl)-2(5H)-furanone (Compound 8).

Example 5

As in Example 4, but substituting phenyl isocyanate with diethyl chlorophosphate, gives 3-(1-diethylphosphonooxytridecyl)-2(5H)-furanone (Compound 22).

Example 6

As in Example 4, but substituting phenyl isocyanate with ethyl chloroformate, gives 3-(1-ethoxycarbonyloxytridecyl)-2(5H)-furanone (compound 9).

Example 7

As in example 4, but substituting phenyl isocyanate with methoxyethyl chloromethyl ether, gives 3-[1-(2-methoxy)ethoxymethoxy]tridecyl-2(5H)-furanone (Compound 23).

Example 8

Reacting 3-(1-hydroxytridecyl)-2-triethylsilylfuran (Compound 20) with diphenylphosphoryl azide and diethyl azidocarboxylate gives 3-(1-azidotridecyl)-2-triethylsilylfuran (Compound 24). Reducing this intermediate with lithium aluminum hydride, followed by acetylation with acetic anhydide gives 3-(1-acetamido tridecyl)-2-triethylsilylfuran (Compound 25). Singlet oxygen oxidation of this amide, under conditions as in Example 1, followed by reduction with sodium borohydride gives 3-(1-acetamidotridecyl)-2(5H)-furanone (Compound 10).

Reducing 3-(1-azidotridecyl)-2-triethylsilylfuran (Compound 24 with lithium aluminum hydride, as in Example 8, followed by reacting the intermediate with methanesulfonyl chloride, gives 3-(1-methanesulfonamidotridecyl)-2-triethylsilylfuran (Compound 26). Oxidizing this sulfonamide, under conditions as in Example 1, followed by reduction with sodium borohydride gives 3-(1-methanesulfonamidotridecyl)-2(5H)-furanone (Compound 11).

What is claimed is:

1. A compound of the formula

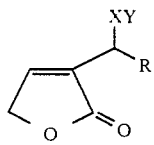

wherein
R is alkyl having 4 to 25 carbons, carbocyclic arylalkyl or alkenyl containing 4 to 25 carbons and one or more olephinic bonds;

X is O, NH or NR$_1$, where R$_1$ is alkyl of 1 to 20 carbons or arylalkyl, and

Y is H, alkyl of 1 t 20 carbons, carbocyclic arylalkyl, carbocyclic aryl, alkenyl containing one or more olephinic bonds and 2 to 20 carbons, PO(OH)$_2$, PO(OH)OR$_2$, PO(OH)R$_2$, PO(OH)R$_2$ PO(OR$_2$)$_2$, where R is independently alkyl of 1 to 20 carbons, phenyl, further Y is CO—R$_3$, CO—OR$_3$, CONHR$_3$, SO$_2$R$_3$, SO$_2$NHR$_3$, (CH$_2$)$_n$—O—R$_3$, or (CH$_2$)$_n$—O—(CH$_2$)$_m$—O—(CH$_2$)$_m$—O—R$_3$,
where n, and m, are integers and are independently 1 to 20 and R$_3$ is H, lower alkyl having 1 to 6 carbons, alkenyl containing one or more olephinic bonds and 2 to 6 carbons, carbocyclic aryl, carbocyclic arylalkyl with the proviso that when Y is CO—OR$_3$ and CONHR$_3$ then R$_3$ is not hydrogen or a pharmaceutically acceptable salt thereof.

2. A compound of claim 1 wherein R is long chain alkyl having 4 to 25 carbons.
3. A compound of claim 2 where R is n-alkyl having 4 to 25 carbons.
4. A compound of claim 1 where X is O.
5. A compound of claim 1 where X is NH.
6. A compound of claim 1 where Y is hydrogen
7. A compound of claim 1 where Y is R$_3$—CO.
8. A compound of claim 1 Y is CONHR$_3$.
9. A compound of claim 1 where Y is PO(OR$_5$)$_2$.
10. A compound of claim 1 where Y is COOR$_3$.
11. A compound of claim 1 where Y is R$_3$SO$_2$.
12. An anti-inflammatory pharmaceutical composition including a pharmaceutically acceptable excipient and an amount effective for alleviating symptoms of inflammatory diseases of a compound set forth in claim 1.

13. A compound of the formula

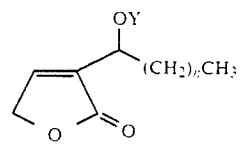

wherein
n is an integer having the value of 4 to 25, and
Y is H, alkyl of 1 to 20 carbons, PO(OH)$_2$, PO(OH)OR$_2$, PO(OH)R$_2$, PO(OR$_2$)$_2$, CO—R$_3$, CO—OR$_3$, CONHR$_3$, or SO$_2$R$_3$, where R$_2$ is independently alkyl of 1 to 20 carbons, and R$_3$ is H, lower alkyl having 1 to 6 carbons, phenyl phenylalkyl, with the proviso that when Y is, CO—OR$_3$, and CONHR$_3$ then R$_3$ is not hydrogen, or a pharmaceutically acceptable salt thereof.

14. A compound of claim 13 where Y is COR$_3$.
15. A compound of claim 14 where Y is COCH$_3$.
16. The compound of claim 15 where n is 7.
17. The compound of claim 15 where n is 11.
18. A compound of claim 13 where Y is hydrogen.
19. The compound of claim 18 where n is 11.
20. A compound of claim 13 where Y is CONHR$_3$.
21. A compound of claim 21 where R$_3$ is phenyl.
22. The compound of claim 21 where n is 11.
23. A compound of claim 13 where Y is COOR$_3$.
24. A compound of claim 23 where R$_3$ is ethyl.
25. The compound of claim 24 where n is 11.
26. A compound of the formula

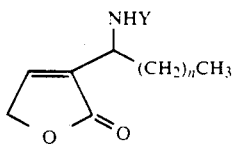

wherein n is an integer having the value of 4 to 25, and
Y is H, alkyl of 1 to 20 carbons, PO(OH)$_2$, PO(OH)OR$_2$, PO(OH)R$_2$, PO(OR$_2$)$_2$, CO—R$_3$, CO—OR$_3$, CONHR$_3$, or SO$_2$R$_3$, where R$_2$ is independently alkyl of 1 to 20 carbons, and R$_3$ is H, lower alkyl having 1 to 6 carbons, phenyl phenylalkyl, with the proviso that when Y is, CO—OR$_3$, and CONHR$_3$ then R$_3$ is not hydrogen or a pharmaceutically acceptable salt thereof.

27. A compound of claim 26 where Y is COR$_3$.
28. A compound of claim 27 where Y is COCH$_3$.
29. The compound of claim 28 where n is 11.
30. A compound of claim 26 where Y is SO$_2$R$_3$.
31. A compound of claim 30 where R$_3$ is methyl.
32. The compound of claim 32 where n is 11.

* * * * *

UNITED STATES PATENT AND TRADEMARK OFFICE
CERTIFICATE OF CORRECTION

PATENT NO. : 5,043,457                                      Page 1 of 3
DATED     : August 27, 1991
INVENTOR(S) : Gary C. M. Lee It is certified that error appears in the above-identified patent and that said Letters Patent is hereby corrected as shown below: ON THE TITLE PAGE:

IN THE ABSTRACT, line 6 after Formula 1, after "bonds" insert —,—;

Column 1, line 27, after "2)" insert —and—;

Column 1, line 29, after "biological" insert —activity—;

Column 2, line 63, "osteoarrhritis" should be —osteoarthritis—;

Column 5, line 4, after "Formula" the "s" should be an —8—;

Column 5, line 37, after "are" insert —the—;

Column 5, line 41, after "atoms.", —The compounds— should start a new paragraph;

Column 5, line 53, after "of" insert —enantiomers—;

Column 6, line 33, "CONHC6H5" should be —$CONHC_6H_5$—;

Column 7, line 31, "anoalide" should be —manoalide—;

Column 7, line 47-48, after "comprise" insert —compounds—;

Column 8, line 59, after "used" insert —for—;

Column 9, line 26, "3 mM" should be —3mM—;

Column 10, line 4, "2. m" should be —2.0 ml—;

Column 10, line 28, after "to" insert —provide—;

Column 10, Reaction Scheme 2, "$(CH_3)_2SiCl$" should be —$(CH_3)_3SiCl$—;

Column 11, line 59, after "scheme" the "z" should be —2—;

Column 13, line 12, after "substituent." insert —In—;

Column 13, line 35, before "in" insert —(—;

Column 14, line 7, after "tetrahydrofuran," insert —in—;

Column 15, line 22, "$R_3SO2Cl$" should be —$R_3SO_2Cl$—;

Column 15, line 69, after "the" (first occurrence) insert —synthetic—;

UNITED STATES PATENT AND TRADEMARK OFFICE
CERTIFICATE OF CORRECTION

PATENT NO. : 5,043,457
DATED : August 27, 1991
INVENTOR(S) : Gary C. M. Lee

It is certified that error appears in the above-identified patent and that said Letters Patent is hereby corrected as shown below:

Column 16, line 33, "triethylsilylfuran" should be —trimethylsilylfuran—;
Column 16, line 43, after "with" insert —ethyl—;
Column 17, line 2, "285 1702" should be —285.1702—;
Column 17, line 19, "6S.9" should be —68.9—;
Column 17, line 25, "triethylsilylfuran" should be —trimethylsilylfuran—;
Column 17, line 47, "tetrahydro furan" should be —tetrahydrofuran—;
Column 18, line 34, before "-5-" change "]" to —)—;
Column 18, line 44, "217" should be —2.17—;
Column 19, line 47, after "24" insert —)—;
Column 20, line 6 (Claim 1), delete "PO(OH)$R_2$" (second occurrence) in that it was printed twice;
Column 20, line 7 (Claim 1), "R" should be —$R_2$—;
Column 20, line 10 (Claim 1), after "-O-" (second occurrence) delete —O-($CH_2$)m— in that it was printed twice; and
Column 20, line 16 (Claim 1) after "CO-$OR_3$" insert —,—.

UNITED STATES PATENT AND TRADEMARK OFFICE
CERTIFICATE OF CORRECTION

PATENT NO. : 5,043,457
DATED : August 27, 1991
INVENTOR(S) : Gary C. M. Lee

It is certified that error appears in the above-identified patent and that said Letters Patent is hereby corrected as shown below:

Column 20, line 16 (Claim 1) after "$CO-OR_3$" insert --,--.

Signed and Sealed this

Tenth Day of August, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO.   :  5,043,457
DATED        :  August 27, 1991
INVENTOR(S)  :  Gary C. M. Lee It is certified that error appears in the above-identified patent and that said Letters Patent is hereby corrected as shown below:

Column 1, line 26, "manolide" should be --manoalide--; and

Column 19, line 40, "anhydide" should be --anhydride--.

Signed and Sealed this

Seventh Day of December, 1993

Attest:

BRUCE LEHMAN

Attesting Officer    Commissioner of Patents and Trademarks